Figure 1:
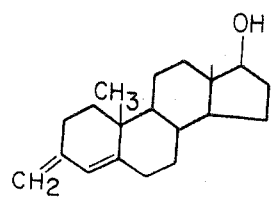
Figure 1:
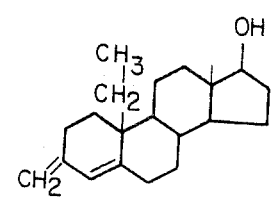
Figure 1:
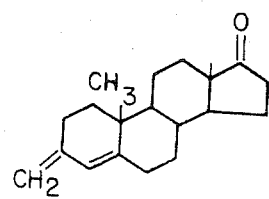
Figure 1:
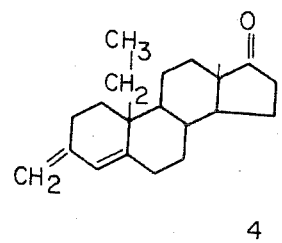

United States Patent [19]

Fishman et al.

[11] Patent Number: 4,546,098
[45] Date of Patent: Oct. 8, 1985

[54] ESTROGEN SYNTHESIS INHIBITORS

[75] Inventors: Jack Fishman; Shinichi Mayairi, both of New York, N.Y.

[73] Assignee: The Rockefeller University, New York, N.Y.

[21] Appl. No.: 600,164

[22] Filed: Apr. 13, 1984

[51] Int. Cl.[4] .......................... A61K 31/56; C07J 1/00
[52] U.S. Cl. ................................ 514/177; 260/397.3; 260/397.4; 260/397.5; 514/178; 514/182
[58] Field of Search ............... 260/397.4, 397.3, 397.5; 424/238; 514/177, 178, 182

[56] References Cited

PUBLICATIONS

Chemical Abstracts, vol. 71 (13) 61686r.

Primary Examiner—Elbert L. Roberts
Attorney, Agent, or Firm—Wyatt, Gerber, Shoup, Scobey and Badie

[57] ABSTRACT

Invention relates to 3-methylene substituted androst-4-ene-17-oxygenated compounds substituted with various substituents at the 10β-position which are useful as inhibitors of estrogen biosynthesis.

15 Claims, 7 Drawing Figures

1

2

3

4

1

2

3

4

ESTROGEN SYNTHESIS INHIBITORS

BACKGROUND OF THE INVENTION

This invention relates to 3-methylene substituted androst-4-ene-17-oxygenated compounds substituted with various substituents at the 10β-position, to their use as inhibitors of estrogen biosynthesis, and to therapeutically useful compositions containing these valuable compounds. The invention also includes within its scope analogous androstene derivatives unsaturated at the 1,2- and/or 6,7-positions. It includes also certain novel intermediates useful for the preparation of the biologically active compounds.

In recent years the mechanism of estrogen biosynthesis has been elucidated. It proceeds via the transformation of the C-19 neutral steroids to the C-18 phenolic estrogens. The aromatization reaction involves expulsion of the angular C-19 methyl group as formic acid and the stereospecific loss of the C-1 and C-2 hydrogens. A complex of microsomal enzymes referred to as aromatase is responsible for these transformations. As this mechanism became understood, the opportunity was presented for designing compounds which would retard the synthesis of estrogen by interfering with the action of aromatase. Such compounds are known as aromatase inhibitors.

Although biosynthesis of estrogen occurs principally in the ovaries and testes, some also occurs in adipose tissue and muscle as well as other tissues. This peripheral aromatization of androgens to estrogens increases after menopause and becomes the main source of estrogens in women. Peripheral aromatization may similarly increase after ovariectomy which is frequently performed for the treatment of breast cancer. Some breast tumors themselves are also reported to synthesize estrogens. In endometrial cancer, peripheral formation of estrogen appears to be important in the etiology of the disease. Thus, inhibition of estrogen production by compounds which could act at all aromatizing sites might be an effective alternative to surgical removal of ovaries and adrenals in patients with breast cancer and a useful treatment for endometrial cancer.

The aromatase inhibitors could also be useful in the treatment of other estrogen related phenomena such as fertility control, gross ceptic disease and benign prostatic hypertrophy.

U.S. Pat. No. 4,235,893 describes certain ester derivatives of 4-hydroxy-4-androstene-3,17-dione as useful for the inhibition of estrogen biosynthesis. U.S. Pat. No. 4,322,416 describes certain 1-alkynyl steroids as aromatase inhibitors.

Other aromatase inhibitors such as ammoglutethimide and cyanoketone are also known, but these compounds interfere with the action of a broad spectrum of enzymes involved in the production of other essential steroid hormones. These steroids must be replaced when such conventional aromatase inhibitors are employed in therapy.

THE INVENTION

It has now been discovered that certain 3-methylene androst-4-enes substituted at the 17-position with a keto, β-hydroxyl, or acylated hydroxyl group and at the 10-position with certain substituents to be described more fully hereinafter, are useful as aromatase inhibitors for the treatment of mammals in need of such treatment.

The novel androst-4-ene compounds of this invention may be represented by the formula:

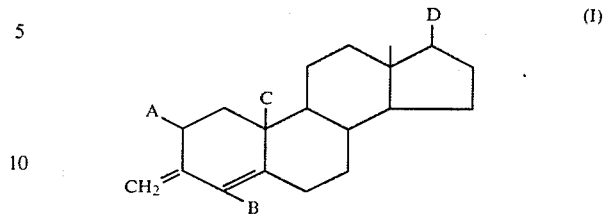

The corresponding $\Delta^{1,4}$, $\Delta^{4,6}$ and $\Delta^{1,4,6}$ compounds are also novel and useful. In the formula A–D represent the following:

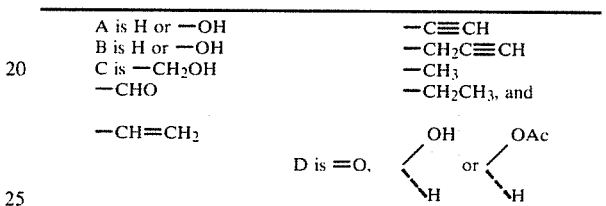

Ac represents an acyl group containing only carbon, hydrogen and oxygen up to a total of six carbon atoms.

It should be noted with respect to the foregoing formula that:

1. A and B cannot both be hydroxyl at the same time,
2. If there is a double bond at the 1,2-position, the group substituted at the 10-position cannot contain an oxygen atom,
3. If there is a double bond at only the 4,5-position and no hydroxyl at the 2 or 4 position, C cannot be methyl or ethyl,
4. If there are double bonds at the 1,2- and 6,7-positions or at the 6,7 position, C must be methyl or ethyl,
5. C can only be an aldehyde group when A and B are hydrogens and the only double bond is at the 4,5-position.

Certain compounds within the scope of the invention are known, but their valuable activity as aromatase inhibitors has not heretofore been reported.

These compounds include those represented by the formula:

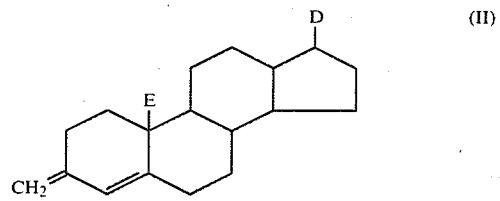

wherein D has the same meaning as above and E is methyl or ethyl.

All of the foregoing compounds may be used alone or together with pharmaceutically acceptable carriers as aromatase inhibitors.

This invention will be best understood by reference to the attached figures which show the formulas for many of the compounds within the scope of the invention.

Compounds of Formula II which are useful for preparing the compositions of the invention and in practicing the method of the invention are shown in FIG. 1. In the figure, the numbers appearing under each formula are for identification purposes.

Compound 1,3-methylene-androst-4-ene-17β-ol is described in Sondheimer et al, J. Am. Chem. Soc. 79, 5029 (1957).

Compound 2,3-methylene-10β-ethyl-estra-4-ene-17β-ol is prepared from the corresponding 3-one by the Wittig reaction. The 3-one is described in Halpern et al, J. Org. Chem., 31, 693 (1966).

Compound 3,3-methylene-androst-4-ene-17-one is described by Evans et al, J. Chem. Soc., 4312 (1963).

Compound 4,3-methylene-10β-ethyl-estra-4-ene-17-one is prepared by oxidation of compound 2, for example, with pyridium dichromate.

The Wittig reaction is conducted by reacting the selected androst-4-ene-3-one with a molar excess of methyltriphenylphosphonium bromide and n-butyl lithium at ambient temperature, e.g. 20° C. to 40° C. in an anhydrous organic solvent, suitably a non-polar solvent such as ether or a saturated hydrocarbon. The reaction is best conducted in an inert atmosphere such as nitrogen. In the first step of the reaction the Wittig reagent is formed by reaction of the n-butyl lithium with the methyltriphenylphosphonium bromide. This normally requires from 15 to 45 minutes. The Wittig reagent then reacts with the steroid substrate to substitute the 3-keto group with a methylene group. The latter reaction typically takes place over a period of from 5 to 20 hours.

The Wittig reaction is well known in organic synthesis for the conversion of cyclic ketones to exocyclic olefins. Those skilled in the art will recognize that many variations are possible from the foregoing general description. For example, the n-butyl lithium can be replaced with phenyl lithium.

Normally a large molar excess of Wittig reagent is employed compared to the steroid substrate to insure as complete a reaction as possible. The excess is readily destroyed by reaction with water.

The presently preferred oxidizing agent for converting the 17β-hydroxyl to a 17-one is pyridinium dichromate, although other oxidizing agents may be employed. These include, for example, chromium trioxide, sodium dichromate, N-bromoacetamide and aluminum isopropoxide or aluminum tert-butoxide in the presence of a hydrogen acceptor such as acetone or cyclohexane in an inert organic solvent such as benzene, toluene or xylene.

The 17β-acyl esters are prepared by conventional procedures, for example by reaction of the corresponding hydroxyl compound with a selected acyl halide or anhydride. In the event that the acyl hydrocarbon group selected is derived from a dicarboxylic acid, it is often advantageous to treat the isolated aromatase inhibitor with a base derived from an alkali metal or alkaline earth metal salt. These bases include, for example, sodium, potassium, or barium hydroxides as well as the corresponding carbonates and bicarbonates. Products so prepared are especially useful because of their increased solubility in water. The primary alcohol function is readily regenerated if desired by hydrolysis, for example with methanolic potassium hydroxide. Typical esters include formates, acetates, propanoates, propenoates, isobutyrates, hemisuccinates and trimethyl acetates.

Products prepared in accordance with the procedures described above may be isolated by conventional means well known to those skilled in the art. These include solvent extraction, crystallization and similar operations. Chromatographic purification is especially useful using any of a wide variety of solvents and eluents including hydrocarbons, halogenated hydrocarbons, esters, ethers and alcohols. Mixed solvents, as is known, are especially convenient. Typical absorbents include alumina and silica-gel.

As the description of this invention proceeds, it will be noted that the reactions and procedures described above will be employed several times. What has been said heretofore is equally applicable to what comes after.

Figure 2:
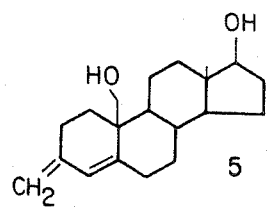
Figure 2:
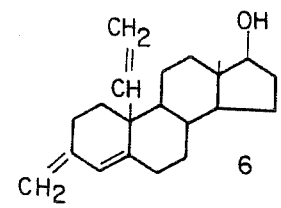
Figure 2:
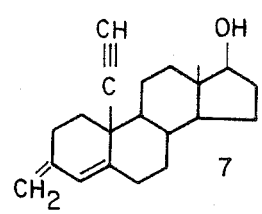
Figure 2:
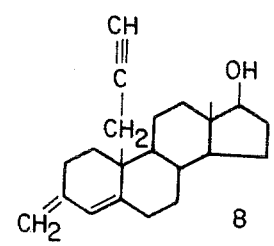
Figure 2:
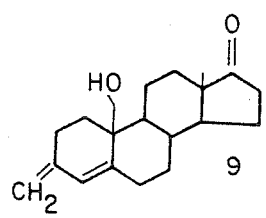
Figure 2:
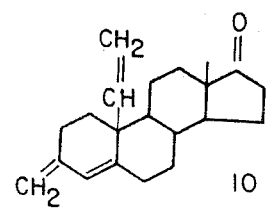
Figure 2:
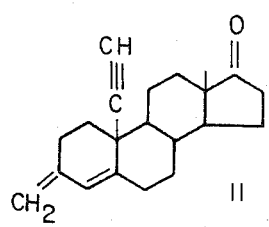
Figure 2:
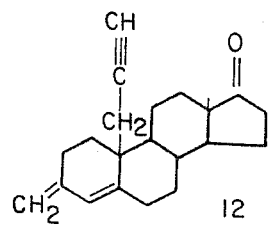

FIG. 2 shows the formulas for certain of the novel Δ⁴-compounds within the scope of this invention.

The starting compound for the preparation of compound 9 which is 3-methylene-androst-4-ene-19-ol-17-one is the acetate of androst-4-ene-19-ol-3,17-dione which is described by Knox et al in J. Org. Chem., 30, 21 98 (1965). The conversion is effected utilizing the Wittig reaction. In the course of the reaction the acetyl group is hydrolyzed. Alternatively, the corresponding 19-hydroxy compound can be utilized as the starting material.

Compound 9 may be converted to compound 5, 3-methylene-androst-4-ene-17β,19-diol by reduction. Any of a number of reducing agents suitable for the conversion of ketones to secondary alcohols can be employed for this reaction. These include, for example, lithium aluminum hydride and sodium borohydride. The latter is preferred. Normally a molar excess of the reducing agent is employed and the excess is destroyed with acetic acid at the end of the reaction.

The Wittig reaction is used to produce compound 11,3-methylene-10β-vinyl-estra-4-ene-17-one from the corresponding 3,17-dione which is described by Halpern et al in J. Org. Chem., 31, 693 (1966). Compound 11 is reduced to produce compound 6,3-methylene-10β-vinyl-estra-4-ene-17β-ol.

The same series of reactions, i.e. Wittig followed by reduction, is used to convert 10β-ethynyl-estra-4-ene-3,17-dione (Marcotte et al, Steroids, 39, 325 (1982)) to produce 3-methylene-10β-ethynyl-estra-4-ene-17-one, compound 11, and then 3-methylene-10β-ethynyl-estra-4-ene-17β-ol, compound 7.

The compound 10β-propargyl-estra-4-ene-3,17-dione which is described by Convey et al in J. Biol. Chem., 256, 1076 (1981) is converted to compound 12, which is 3-methylene-10β-propargyl-estra-4-ene-17-one. This latter compound is reduced to form 3-methylene-10β-propargyl-estra-4-ene-17β-ol, compound 8.

Figure 3:
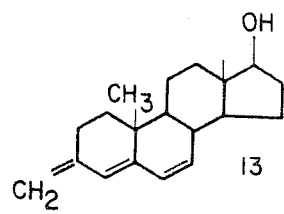
Figure 3:
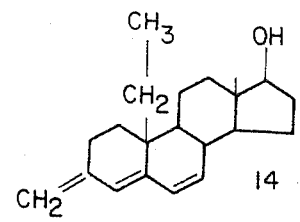
Figure 3:
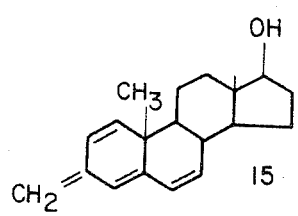
Figure 3:
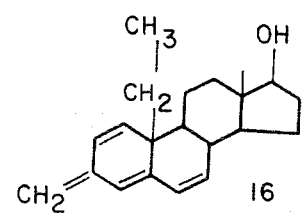
Figure 3:
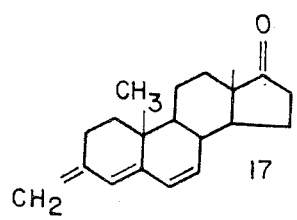
Figure 3:
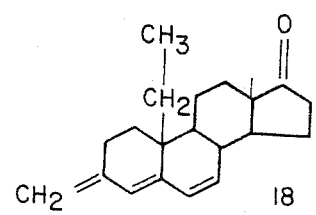
Figure 3:
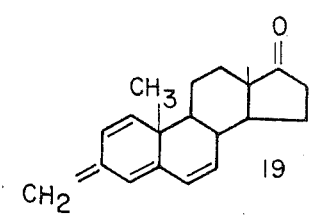
Figure 3:
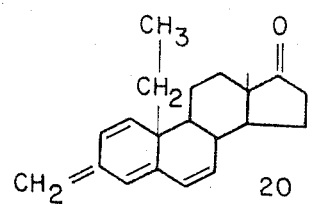

FIG. 3 shows the formulas for certain of the novel Δ¹,⁴, Δ⁴,⁶ and the Δ¹,⁴,⁶ compounds of this invention.

The compound androst-4,6-diene-3,17-dione is described by Djerassi et al in J. Am. Chem. Soc., 72, 4534 (1950). It can be converted to 3-methylene-androst-4,6-diene-17-one, compound 17 by the Wittig reaction. Reduction of compound 17, for example with sodium borohydride, produces compound 13,3-methylene-androst-4,6-diene-17β-ol.

Kaufman et al describes androst-1,4,6-triene-3,17-dione in J. Am. Chem. Soc., 72, 4531 (1950). It can be converted to 3-methylene-androst-1,4,6-triene-17-one, compound 19 by the Wittig reaction, and this compound in turn is reduced to compound 15,3-methylene-androst-1,4,6-triene-17β-ol.

The starting compound for the production of compounds 14 and 18 is 10β-ethyl-estra-4-ene-3,17dione (Halpen et al, cited above). This compound may be converted to 10β-ethyl-estra-4,6-dien-3,17-dione by oxidation with a quinone having an oxidation-reduction potential less than −0.5, preferably −0.65 or less, at a temperature between 70° C. and 190° C. in an inert organic solvent having a boiling point of at least about 70° C. About 1 to 3 moles of quinone per mol of steroid is employed.

Oxidation-reduction potentials are readily determined by reference to any scientific texts (See Handbook of Chemistry and Physics, 58st edition, page D-141, Chemical Rubber Company, 1978, and Latimer and Hildebrand, Reference Book of Inorganic Chemistry, rev. ed., pages 474–481, MacMillan Company, 1940). Quinone itself (also known as benzoquinone), chloranil or tetrachloroquinone, toluquinone or methylquinone, 1,2-naphthaquinone, 2-6-dichlorobenzoquinone, hydroquinone and xyloquinone or dimethylquinone, are useful.

Typically useful solvents include mononuclear aromatic hydrocarbons, mononuclear halogenated aromatic hyrocarbons, oxygenated polar alicyclic organic solvents and oxygenated polar aliphatic solvents. Specific solvents include t-butanol, hexanol, xylene and acetic acid. The reaction is described in detail in U.S. Pat. No. 2,836,607 and by Agnello et al in J. Am. Chem. Soc., 82, 4293 (1960).

Compound 18,3-methylene-10β-ethyl-estra-4,6-dien-17-one, is obtained by subjecting 10β-ethyl-estra-4,6-diene-3,17-dione to the Wittig reaction.

Compound 18 is reduced, for example, with sodium borohydride to produce compound 14,3-methylene-10β-ethyl-estra-4,6-dien-17β-ol.

Two procedures are available for the production of Δ$^{1,4,6}$-trienes substituted with a 10β-ethyl group. One is to use selenium dioxide to convert 10β-ethyl-estra-4,6-diene-3,17-dione to 10β-ethyl-1,4,6-triene-3,17-dione. Another is to use a large molar excess of chloranil or equivalent quinone to convert the Δ$^4$-compound to the Δ$^{1,4,6}$-compound.

A double bond can be introduced at the 1,2-position of Δ$^4$-steroids by reaction with selenium dioxide in an inert organic solvent at an elevated temperature. Solvents which are useful for this reaction include, for example, tert-butanol, benzene, ethylene, xylene, dioxane and dibutyl cellosolve. Preferred conditions include the addition of a lower aliphatic acid, particularly acetic acid, to a tertiary butanol mixture. The reaction temperature is from about 75° C. to 200° C., and reaction is normally continued for from about two to eight hours. Generally several molecular proportions of selenium dioxide are added during the reaction period. The reaction is more fully described and illustrated in U.S. Pat. No. 2,877,239, and by Bowers et al in J. Am. Chem. Soc., 81, 5991 (1959).

For the preparation of some of the compounds within the scope of this invention utilizing the selenium dioxide reaction it is best that free hydroxyl groups be acylated with an acyl hydrocarbon group of the nature described above. The protecting group can be readily removed by acid or alkaline hydrolysis in aqueous media.

In order to produce Δ$^{1,4,6}$-compounds from Δ$^4$ compounds the quinone procedures described above can be employed under the disclosed conditions except that a large excess of quinone, e.g. 3 to 6 moles per mol of steroid substrate is employed. The procedure is described in the Agnello article referred to above, and in U.S. Pat. No. 2,992,216.

The compounds prepared by these procedures are compound 20,3-methylene-10β-ethyl-estra-1,4,6-triene-17-one and compound 16,3-methylene-10β-ethyl-estra-1,4,6-triene-17β-ol.

Those skilled in the art will recognize that it is possible to apply the selenium dioxide and quinone reactions to 3-keto compounds to produce androstene derivatives with the desired substituents at the 10β-position and then to employ the Wittig reaction to place the 3-methylene group. For example, 10β-ethyl-estra-1,4,6-triene-3,17-dione can be produced and subjected to the Wittig reaction. Reduction of a carbonyl group at the 17 position is performed with sodium borohydride.

Figure 4:
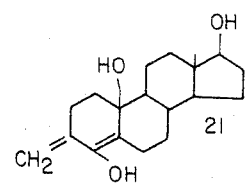
Figure 4:
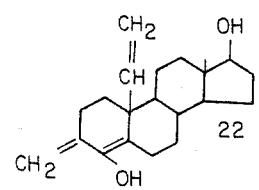
Figure 4:
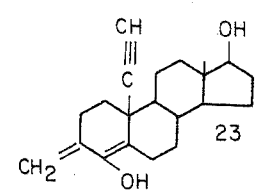
Figure 4:
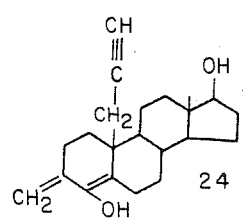
Figure 4:
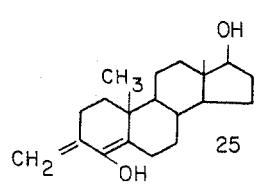
Figure 4:
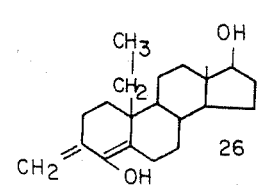
Figure 4:
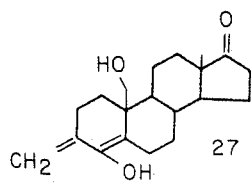
Figure 4:
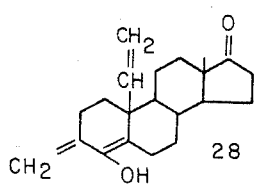
Figure 4:
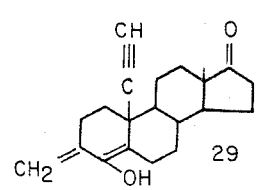
Figure 4:
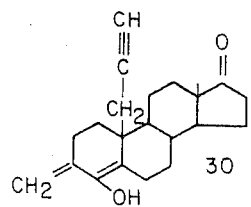
Figure 4:
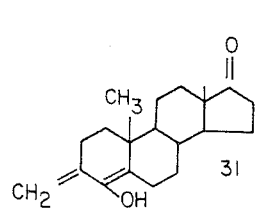
Figure 4:
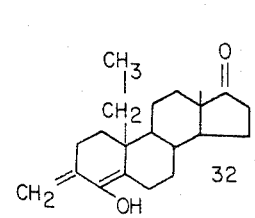

FIG. 4 illustrates novel 4-hydroxyl compounds within the scope of the invention.

Compounds 25, 26, 31 and 32 can all be prepared from the corresponding 3,17-diones. Sources of these compounds are identified hereinabove. The 4-hydroxyl group can be substituted on these 3-keto steroids by the auto-oxidation procedure described by Camerino et al in Tetrahedron Letters, 16, 554 (1961). The 3-keto compounds are first reduced to a mixture of 4,5-dihydro derivated by Pd/C reduction.

The dihydro compounds are dissolved in tert-butanol containing potassium tert-butoxide and left at room temperature, i.e. 20° to 40° C., for about 18 to 50 hours. The reaction can be followed by observing the increase in the U.V. maximum at 278 nm. The Wittig reaction can be selectively applied to 3,17-diones to replace only the 3-keto group with a methylene group. The resulting compounds are reduced with borohydride.

The compounds prepared by these procedures are:

Compound 22—3-methylene-10β-vinyl-estra-4-ene-4,17β-diol.

Compound 23—3-methylene-10β-ethynyl-estra-4-ene-4,17β-diol.

Compound 24—3-methylene-10β-proparycyl-estra-4-ene-4,17-diol.

Compound 25—3-methylene-androst-4-ene-4,17β-diol.

Compound 26—3-methylene-10β-ethyl-estra-4-ene-4,17β-diol.

Compound 28—3-methylene-10β-vinyl-estra-4-ene-4-ol-17-one.

Compound 29—3-methylene-10β-ethynyl-estra-4-ene-4-ol-17-one.

Compound 30—3-methylene-10β-propargyl-estra-4-ene-4-ol-17-one.

Compound 31—3-methylene-androst-4-ene-4-ol-17-one.

Compound 32—3-methylene-10β-ethyl-estra-4-ene-4-ol-17-one.

Compounds 25 and 31 can also be prepared from androst-4-ene-4-ol-3,17-dione 4-acetate. See Brodie et al, Biology of Reproduction 18, 365 (1978). The reaction sequence is, Wittig followed by reduction. The acetoxy group is removed during the Wittig reaction.

Morisawa et al having described the compound androst-4-ene-4,17β,19-triol-3-one 17-acetate in Chem. Pharm. Bull, 17, 1206 (1969). This can be converted to androst-4-ene-4,19-diol-3,17-dione by conventional procedures, subjected to the Wittig reaction and then reduced with sodium borohydride. The compounds prepared in this procedure are compound 21,3-methylene-androst-4-ene-4,17β,19-thiol and compound 27,3-methylene-androst-4-ene-4,19-diol-17-one.

Figure 5:
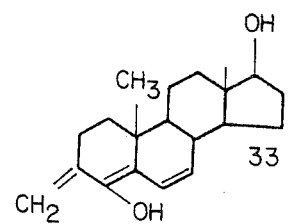
Figure 5:
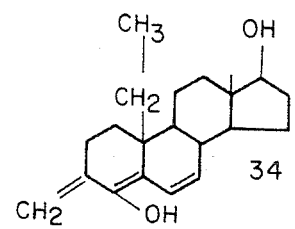
Figure 5:
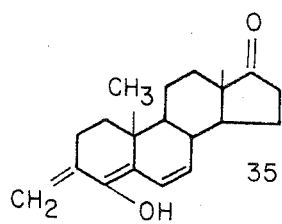
Figure 5:
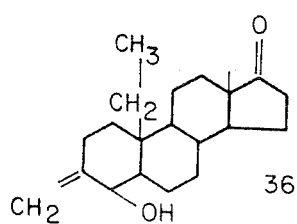

FIG. 5 shows the formulas for novel 4-hydroxyl-Δ[4,6]-compounds of the invention.

Marsh et al in Biochem. Pharm., 31, 701 (1982) describes androst-4,6-diene-4-ol-3,17-dione. This compound can be acetylated to protect the 4-hydroxyl group and then subjected to the Wittig reaction to selectively replace the 3-keto group while concurrently hydrolyzing the acetoxy group to produce compound 35,3-methylene-androst-4,6-diene-4-ol-17-one. Reduction of this compound, for example, with sodium borohydride, provides compound 33, 3-methylene-androst-4,6-diene-4,17β-diol.

Placement of a 4-hydroxyl group on the known compound 10β-ethyl-estra-4-ene-3,17-dione (Halpern et al, cited above) using the procedure of Camerino et al described above affords the novel intermediate 10β-ethyl-estra-4,6-diene-4-ol-3,17-dione. Acetylation of this compound followed by the Wittig reaction and borohydride reduction produces successively:

Compound 36—3-methylene-10β-ethyl-estra-4,6-diene-4-ol-17-one, and

Compound 34—3-methylene-10β-ethyl-estra-4,6-diene-4,17β-diol.

Figure 6:
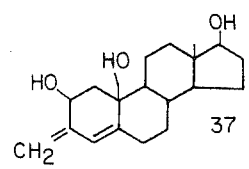
Figure 6:
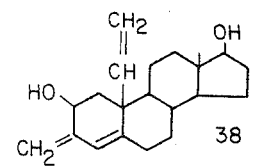
Figure 6:
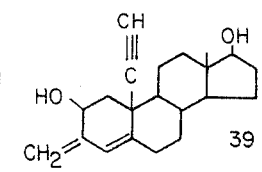
Figure 6:
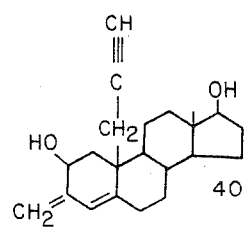
Figure 6:
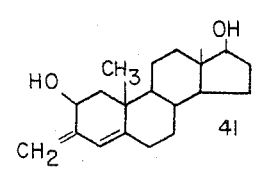
Figure 6:
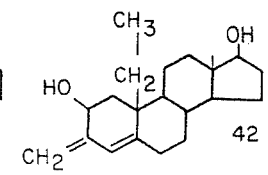
Figure 6:
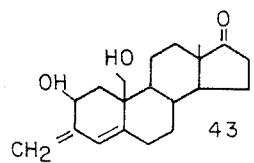
Figure 6:
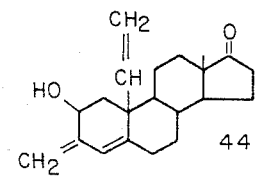
Figure 6:
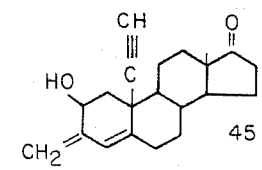
Figure 6:
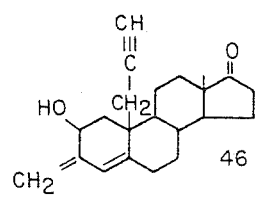
Figure 6:
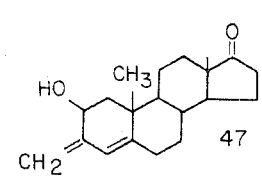
Figure 6:
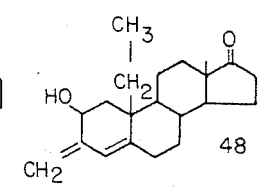

Novel 2-hydroxyl compounds within the scope of the invention are shown in FIG. 6.

Androst-4-ene-2β,19-diol-3,17-dione 2,19-diacetate is described by Hosoda et al, J. Am. Chem. Soc. 96, 7325 (1974). This compound can be converted successively to compound 43, 3-methylene-androst-4-ene-2β,19-diol-17-one and 3-methylene-androst-4-ene-2β,17β,19-triol, compound 37 by the Wittig reaction followed by borohydride reduction.

The compound 10β-vinyl-estra-4-ene-3,17-dione described by Halpern et al, cited above is converted to 10β-vinyl-estra-4-ene-2β-ol-3,17-dione acetate by reaction with a molar excess of lead tetraacetate at 60° to 120° C. in acetic acid or under reflux in benzene for a reaction period of from 6 to 15 hours. This can be converted to 3-methylene-10β-vinyl-estra-4-ene-2-ol-17-one, compound 44, by the Wittig reaction. The latter compound may be reduced with sodium borohydride to produce compound 38, 3-methylene-10β-vinyl-estra-4-ene-2β, 17β-diol.

A similar series of reactions may be employed starting with the known 10β-ethynyl-estra-4-ene-3,17-dione (Marcotte et al, cited above) to produce successively the novel 10β-ethynyl-estra-4-ene-2β-ol-3,17-dione, followed by:

Compound 45—3-methylene-10β-ethynyl-estra-4-ene-2β-ol-17-one, and

Compound 39—3-methylene-10β-ethynyl-estra-4ene-2β,17β-diol.

The compound 10β-propargyl-estra-4-ene-3,17dione described by Covey, et al, cited above may be converted successively by the same series of reactions to the novel 10β-propargyl-estra-4-ene-2β-ol-3,17-dione, and then to compound 46, 3-methylene-10β-propargyl-estra-4-ene-2β-ol-17-one and Compound 40, 3-methylene-10β-propargyl-estra-4-ene-2β,17β-diol.

Androst-4-ene-2β-ol-3,17-dione has been described by Rao et al, J. Org. Chem., 28, 170 (1963). This compound can be converted to Compound 47, 3-methylene-androst-4-ene-2β-ol-17-one by the Wittig reaction. Compound 47 may then be reduced to compound 41, 3-methylene-androst-4-ene-2β,17β-diol.

The novel intermediate 10β-ethyl-estra-4-ene-2β-ol-3,17-dione may be produced by the lead tetraacetate reaction followed by hydrolysis as described above.

The Wittig reaction followed by borohydride reduction produces, successively:

Compound 48—3-methylene-10β-ethyl-estra-4-ene-2β-ol-17-one, and

Compound 42—3-methylene-10β-ethyl-estra-4-ene-2β,17β-ol.

Figure 7:
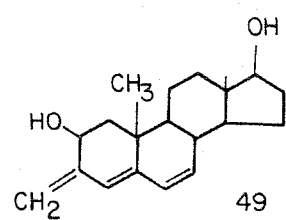
Figure 7:
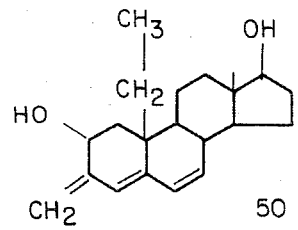
Figure 7:
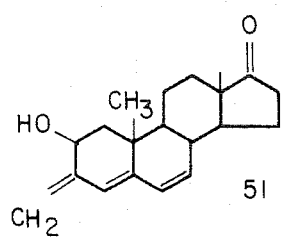
Figure 7:
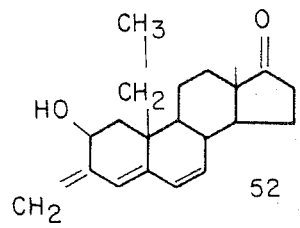

Certain of the 2β-hydroxy-Δ[4,6]-compounds of the invention are shown in FIG. 7.

Compound 49, 3-methylene-androst-4,6-diene-2β,17β-diol can be produced by acetylation of androst-4-ene-2β-ol-17-one described above, followed by oxidation at the 6,7-position with chloranil or an equivalent quinone to produce the novel intermediate androst-4,6-diene-2β-ol-17-one 2-acetate. This compound when subjected to the Wittig reaction, affords compound 51, 3-methylene-androst-4,6-diene-2β-ol-17-one. Reduction of compound 51 provides compound 49, 3-methylene-androst-4,6-diene-2β,17β-diol.

A similar series of reactions with 10β-ethyl-estra-4-ene-2β-ol-17-one produces successively:

10β-ethyl-estra-4,6-diene-2β-ol-17-one 2-acetate,

Compound 52—3-methylene-10β-ethyl-estra-4,6-diene-2β-ol-17-one, and

Compound 50—3-methylene-10β-ethyl-estra-4,6-diene-2β,17-diol.

The biologically active compounds of this invention may be administered alone or in combination with acceptable pharmaceutical carriers, the choice of which is determined by the preferred route of administration, the solubility of the compound and standard pharmaceutical practice. For oral administration the compounds may be administered in the form of tablets containing excipients such as starch or milk sugar. Aqueous solutions and elixirs which may be sweetened or flavored may also be used. For intra-articular injection aqueous suspensions may be employed. In this case various suspending and wetting agents may be added to the composition to obtain a suspension not tending to settle out easily or to pack down in the bottle in which it is stored. Intramuscular and subcutaneous dosage forms may also be prepared by standard pharmaceutical practice.

The following examples are given solely for the purpose of illustration and are not to be construed as limitations of this invention, many apparant variations of which are possible without departing from the spirit or scope thereof.

EXAMPLE 1

A mixture of [19,19,19-$^3$H]androst-4-ene-3,17-dione diluted with cold androstenedione ($2.8 \times 10^6$ dpm, 4 n mole) and an inhibitor (4 n mole) in ethanol (50 μl) was incubated with 5 ml of a placental microsomes (1 mg/ml of 0.05M tris-HCl, pH 7.2) in the presence of NADPH (5 mg), glucose-6-phosphate (2.5 mg), and glucose-6-phosphate dehydrogenase (3.1 units). The incubations were carried out at 37° C. for 30 minutes in air. A control incubation was carried out as above except that the inhibitor was excluded. The incubation mixture (1 ml) was mixed with 1M phosphoric acid (1 ml), flash frozen and lyophilized. Radioactivity in 0.5 ml of the distilled component was measured (A). And 1.2 ml of the distilled component was mixed with 0.3 ml of 1N sodium hydroxide, flash frozen, and lyophilized. Radioactivity in 0.5 ml of the distilled water was measured (B).

Formic Acid $= A - B \times 1.25$

The results are shown in the following table.

| INHIBITION OF FORMIC ACID FORMATION BY 3-METHYLENE COMPOUNDS | |
|---|---|
| | % Inhibition |
| Control | 0 |
| 3-Methylene-androst-4-en-17-one (Cmpd. 3) | 86 |
| 3-Methylene-androst-4-en-17-ol (Cmpd. 1) | 43 |
| 3-Methylene-androst-4-en-19-ol-17-one (Cmpd. 9) | 90 |
| 3-Methylene-androst-4-ene-17,19-diol (Cmpd 5) | 55 |
| 3-Methylene-androst-4-ene-17,19-dione (Cmpd. 53) | 70 |

Similar results are obtained with other aromatase inhibitors of this invention.

EXAMPLE 2

3-Methylene-androst-4-ene-19-ol-17-one—Compound 9

To a solution of methyltriphenylphosphonium bromide (8 m mol) in anhydrous ether, n-butyl lithium (8 m mol) in n-hexane was added slowly with stirring at room temperature under nitrogen. The mixture was stirred for 20 minutes, androst-4-ene-19-ol-3,17-dione 19-acetate (1 m mol) dissolved in anhydrous ether was added, and the mixture stirred overnight. The ether was removed by distillation under nitrogen, and replaced by anhydrous tetrahydrofuran. The mixture was refluxed for 1.5 hours, diluted with chilled water, extracted with ethyl acetate, washed with water, dried over anhydrous sodium sulfate, filtered, and evaporated under vacuum. The product was purified by silica gel chromatography using n-hexane-ethyl acetate as a solvent.

The following compounds are similarly prepared from the compounds described in the specification:
Compounds 9 through 12
Compounds 17 through 20
Compounds 25 through 32
Compounds 35 and 36
Compounds 43 through 48
Compounds 51 and 52.

EXAMPLE 3

3-Methylene-Androst-4-ene-17β,19-dione—Compound 53

To 3-methylene androst-4-en-19-ol-17-one (40 mg) in methylene chloride (5 ml) was added a molar excess of pyridinium dichromate and the mixture was stirred at room temperature for 2 hours. The resultant mixture was diluted with ether, passed through silica gel on a sintered glass funnel, and evaporated down. 3-Methylene-androst-4-ene-17,19-dione was purified by silica gel column chromatography using n-hexane-ethyl acetate as a solvent.

EXAMPLE 4

3-Methylene-androst-4-ene-17β,19-diol—Compound 5

To a solution of 3-methylene-androst-4-ene-19-ol-17-one in methanol was added a 2 molar excess of sodium borohydride. The mixture was stirred overnight at room temperature, diluted with water, extracted with ethyl acetate, washed with water, the organic layer separated, and dried over anhydrous sodium sulfate, filtered and evaporated. The residue was purified by thick layer chromatography over silica gel using n-hexane-ethyl acetate as a solvent.

The following compounds are similarly prepared from starting materials prepared as described in the specification or foregoing examples.
Compounds 5 through 8
Compounds 13 through 16
Compounds 21 through 26
Compounds 33 and 34
Compounds 37 through 42
Compounds 49 and 50.

EXAMPLE 5

3-Methylene-10β-Ethyl-estra-4,6-diene-17-one—Compound 18

290 mg of 10β-ethyl-estra-4-ene-3,17-dione and 594 mg of chloranil are taken up in 15 ml of toluene. The mixture is refluxed for 20 hours in an atmosphere of nitrogen. The solvent is washed with several small portions of 5% sodium hydroxide and then with water. It is dried over anhydrous sodium sulfate for several hours. The solution is filtered and the solvent removed under vacuum. The amorphous solid obtained is triturated with ether, filtered and purified by chromatography over silica gel using a n-hexane-ethyl acetate solvent.

This example illustrates the preparation of $\Delta^{4,6}$-compounds of this invention including those useful as intermediates. To prepare the corresponding $\Delta^{1,4,6}$ compound, the procedure is repeated except that 875 mg of chloranil is employed.

The $\Delta^{4,6}$- or $\Delta^{1,4,6}$-compound is subjected to the Wittig reaction as described in Example 2.

EXAMPLE 6

3-Methylene-10β-vinyl-estra-4-ene-4-ol-17-one—Compound 28

This example illustrates the application of the procedure of Camerino et al to the preparation of compounds of this invention. The known starting material is 10β-vinyl-estra-4-ene-3,17-dione.

277 mg of the starting compound is taken up in 5 ml of methanol and hydrogenated over 30 mg of 5% palladium on charcoal. The catalyst is removed by filtration and the solvent removed under vacuum. The residue is taken up in 10 ml of t-butanol containing 20 mg of potassium t-butoxide and left at room temperature for 36 hours. The solvent is removed under vacuum, the residue taken up in 10 ml of anhydrous ether, filtered, The solution is subjected to the Wittig reaction as described in Example 2.

Similar procedures are employed to produce compounds 29 through 32.

EXAMPLE 7

3-Methylene-androst-1,4-dien-17β-ol-acetate—Compound 15

This procedure illustrates the use of selenium dioxide to product compounds of this invention which are unsaturated at the 1,2-position.

A mixture of 300 mg of androst-4-ene-17β-ol-3-one 17-acetate and 100 mg of selenium dioxide is refluxed in 25 ml of acetic acid. At the end of 2 hours an additional 100 mg of selenium dioxide is added. Refluxing is continued for an additional 3 hours and the reaction mixture filtered through a diatomaceous earth filter aid. The acetic acid is removed under vacuum to leave the desired product as a residue. It is triturated with ether and purified by chromatography over silica gel using a n-hexane-ethyl acetate solvent.

Then the $\Delta^{1,4}$-compound is subjected to the Wittig reaction as described in Example 2.

A similar procedure is employed to prepare the corresponding 10β-ethyl compound which is compound 20.

EXAMPLE 8

3-Methylene-10β-vinyl-estra-4-ene-2β-ol-17-one—Compound 44

This example illustrates the preparation of 2β-hydroxy compounds within the scope of this invention by the sequence of reactions in which the 2β-hydroxyl group is introduced as the acetate with lead tetraacetate.

342 mg of 10β-vinyl-estra-4-ene-3,17-dione in 10 ml of acetic acid is refluxed for 6 hours with 450 mg of lead tetraacetate. The reaction mixture is cooled, diluted with water, extracted with ethyl acetate, washed successively with 0.1N sodium hydroxide, 0.1N hydrochloric acid, 5% sodium bicarbonate and water. The organic solution is dried over anhydrous sodium sulfate, filtered, and the solvent removed under vacuum. The residue is purified chromatographically over silica gel using n-hexane-ethyl acetate solvent.

The product which is obtained as the 2β-acetate is subjected to the Wittig reaction as described in Example 2. The acetyl group is hydrolyzed in the course of the reaction.

EXAMPLE 9

A variety of esters of the 2,4 or 17,19 hydroxy group substituted steroids prepared as described above are prepared in accordance with standard procedures. These include the acetate, isobutyrate, propionate and hemisuccinate. Alkali metal and alkaline earth metal salts of the acid esters are prepared by treatment of the acid ester with molar proportions of a base such as sodium or potassium bicarbonate or barium hydroxide.

The free hydroxyl compounds are prepared from the esters by hydrolysis using one molar portion of potassium carbonate in 10% aqueous methanol solution. The mixture is stirred at room temperature and then poured into ice water to precipitate the desired products.

EXAMPLE 10

| Tablet Formulation | |
|---|---|
| | Mg/tablet |
| Formula: | |
| 3-Methylene-androst-4-ene-17-one | 100.00 |
| Citric acid | 1.00 |
| Lactose | 33.00 |
| Dicalcium phosphate | 70.00 |
| Pluronic, F-68 | 30.00 |
| Sodium Lauryl sulfate | 15.00 |
| Polyvinylpyrrolidone | 15.00 |
| Carbowax 1500 | 5.00 |
| 3A alcohol 50 ml./1000 tablets | |
| Corn starch | 30.00 |
| Dry: | |
| Sodium lauryl sulfate | 3.00 |
| Magnesium stearate | 3.00 |
| Tablet weight | 350.00 |

Procedure.—Mix together the 3-methylene-androst-4-ene-17-one, citric acid, Pluronic F-68, sodium lauryl sulfate, lactose and dicalcium phosphate. Screen through No. 60 mesh screen. Granulate the screened mix with an alcoholic solution containing the polyvinylpyrrolidone, Carbowax 1500 and 6000. Add additional alcohol, if necessary, to bring powder mix to a pasty mass. Add corn starch and continue mixing until uniform damp granules are formed. Pass the damp granulation through a No. 10 screen and dry in an oven at 100° C. for 12-14 hours. Screen the dried granulation using a No. 16 screen, add sodium lauryl sulfate and magnesium stearate, mix and compress on a tablet machine to specifications.

EXAMPLE 11

| Capsule Formulation | |
|---|---|
| Formula: | Mg./capsule |
| 3-Methylene-androst-4-ene-17β,19-diol 17,19-diacetate | 100.00 |
| Citric acid | 1.00 |
| Pluronic F-68 | 40.00 |
| Sodium lauryl sulfate | 20.00 |
| Lactose | 238.00 |
| Magnesium stearate | 1.00 |

Procedure.—Mix together the 3-methylene-androst-4-ene-17β,19-diol 17,19-diacetate, citric acid, Pluronic F-68, sodium lauryl sulfate and lactose. Pass through a No. 80 screen. Add the magnesium stearate, mix and encapsulate into the proper size 2-piece gelatin capsule.

EXAMPLE 12

| Parenteral Formulation | | |
|---|---|---|
| Formula: | | |
| sodium 3-methylene-androst-4,6-diene-17 β-ol 17-hemisuccinate | mg/10 ml | 200 |
| Benzyl alcohol, UF | mg/10 ml | 50.0 |
| Methyl paraben, USP | mg/10 ml | 18.0 |
| Propyl paraben, USP | mg/10 ml | 2.0 |
| Water | ml | 10 |

Procedure.—Dissolve the parabens in approximately 8.5 ml of water at 60° to 70° C. Cool the solution to 40° C. and add the benzyl alcohol. Cool the resultant solution to room temperature and dissolve the sodium 3-methylene-androst-4,6-diene-17β-ol 17-hemisuccinate. Filter the solution through a sterilizing filter into a sterile receptacle. Fill suitably sized vials with the solution, cap loosely and autoclave for one-half hour at 121° C. (15 p.s.i.g.). Each milliliter of this formulation delivers 20 mgs. of active compound.

What is claimed is:

1. A compound selected from the group consisting of compounds represented by the formula:

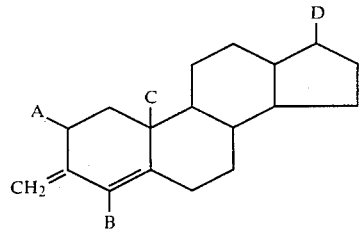

and the corresponding $\Delta^1$ and $\Delta^{1,6}$ compounds wherein:

A is H or β —OH
B is H or OH
C is —CH$_2$OH  —C≡CH
—CHO  —CH$_2$C≡CH

-continued

| —CH=CH₂ | —CH₃<br>—CH₂CH₃, |

D is =O, 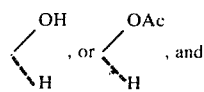, and

Ac is an acyl group containing only carbon, hydrogen and oxygen up to a total of six carbon atoms, provided that
1. A and B are not hydroxyl on the same molecule,
2. When there is a double bond at the 1,2-position, the group substituted at the 10-position does not contain an oxygen atom,
3. When the only double bond is at the 4,5-position and A and B are both hydrogen, C is not methyl or ethyl,
4. When there are double bonds at the 1,2 and 6,7-positions or at the 6,7-position, C is methyl or ethyl,
5. When C is —CHO, A and B are both hydrogen and the only double bond is at the 4,5-position.

2. A pharmaceutical composition comprising a pharmaceutically acceptable carrier and a compound selected from the group consisting of compounds represented by the formula:

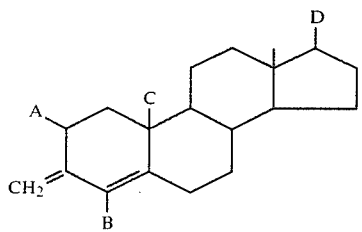

and the corresponding Δ¹,⁴, Δ⁴,⁶ and Δ¹,⁴,⁶ compounds wherein:

| A is H or β —OH | |
|---|---|
| B is H or OH | |
| C is —CH₂OH | —C≡CH |
| —CHO | —CH₂C≡CH |
| | —CH₃ |
| —CH=CH₂ | —CH₂CH₃. |

D is =O 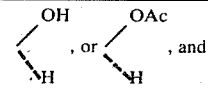, and

Ac is an acyl group containing only carbon, hydrogen and oxygen up to a total of six carbon atoms, provided that:
1. A and B are not hydroxyl on the same molecule,
2. When there is a double bond at the 1,2-position, the group substituted at the 10-position does not contain an oxygen atom,
3. When the only double bond is at the 4,5-position and A and B are both hydrogen, C is not methyl or ethyl,
4. When there are double bonds at the 1,2- and 6,7-position or at the 6,7-position, C is methyl or ethyl,
5. When C is —CHO, A and B are both hydrogen and the only double bond is at the 4,5-position.

3. A pharmaceutical composition comprising a pharmaceutically acceptable carrier and a compound selected from the group consisting of compounds represented by the formula:

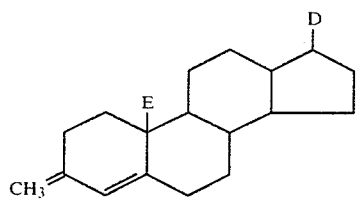

wherein E is methyl or ethyl,
D is =O,

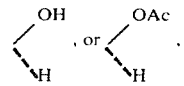

and Ac is an acyl group containing only carbon, hydrogen and oxygen up to a total of six carbon atoms.

4. 10β-Ethyl-estra-4,6-diene-4-ol-3,17-dione.
5. 10β-Ethynyl-estra-4-ene-2β-ol-3,17-dione.
6. 10β-Propargyl-estra-4-ene-2β-ol-3,17-dione.
7. Androst-4-ene-2β,19-diol-3,17-dione.
8. 10β-Ethyl-estra-4-ene-2β-ol-3,17-dione.
9. Androst-4,6-diene-2β-ol-17-one-2-acetate.
10. 10β-Ethyl-estra-4,6-diene-2β-ol-17-one 2-acetate.
11. 3-Methylene-androst-4-ene-17β,19-diol.
12. 3-Methylene-androst-4-ene-2β,19-diol-17-one.
13. 3-Methylene-10β-propargyl-estra-4-ene-17-one.
14. 3-Methylene-androst-4-ene-4-ol-17-one.
15. 3-Methylene-androst-4,6-diene-17-one.

* * * * *